(12) United States Patent
Wright

(10) Patent No.: US 6,213,768 B1
(45) Date of Patent: Apr. 10, 2001

(54) GAG-PREVENTIVE DENTAL IMPRESSION TRAY

(76) Inventor: Carolyn S. Wright, 25 Westerly Dr., Fredonia, NY (US) 14063

( * ) Notice: Subject to any disclaimer, the term of this patent is extended or adjusted under 35 U.S.C. 154(b) by 0 days.

(21) Appl. No.: 09/543,954

(22) Filed: Apr. 6, 2000

Related U.S. Application Data

(63) Continuation-in-part of application No. 09/302,325, filed on Apr. 29, 1999, now abandoned.

(51) Int. Cl.[7] ........................................ A61C 9/00
(52) U.S. Cl. ........................ 433/37; 433/41; 433/42
(58) Field of Search ................ 433/37, 41, 42, 433/43, 44, 45, 46, 47, 48

(56) References Cited

U.S. PATENT DOCUMENTS

| 637,480 | * | 11/1899 | Osgood | 433/37 |
|---|---|---|---|---|
| 1,185,518 | * | 5/1916 | Marcoux | 433/37 |
| 5,478,235 | * | 12/1995 | Schuldt et al. | 433/37 |
| 5,890,895 | * | 4/1999 | Tucker | 433/37 |
| 6,017,217 | * | 1/2000 | Wittrock | 433/37 |
| 6,079,977 | * | 6/2000 | Pericheti | 433/37 |

FOREIGN PATENT DOCUMENTS

| 3837585A1 | * | 5/1990 | (DE) | 433/37 |
|---|---|---|---|---|
| 3904699C1 | * | 7/1990 | (DE) | 433/37 |
| 517967 | * | 11/1955 | (FR) | 433/37 |

OTHER PUBLICATIONS

Alfred Nelson, Can Accurate impressions be obtained with inaccurate impression trays?, Journal of Dental Research, Jan. 1937.*

* cited by examiner

*Primary Examiner*—John J. Wilson
*Assistant Examiner*—Robyn Kieu Doan
(74) *Attorney, Agent, or Firm*—Simpson, Simpson & Snyder, L.L.P.

(57) ABSTRACT

A dental impression tray having a continuous peripheral wall, including an anterior section which conforms generally to the anatomy of a person's maxillary dentition, and a posterior section having a height which is substantially less than that of the anterior wall section, and a floor adjoining the continuous peripheral wall, the floor having a substantially flat portion of arched plan shape, and an elevated portion which conforms generally to the anatomy of the person's hard palate.

10 Claims, 4 Drawing Sheets

GAG-PREVENTIVE DENTAL IMPRESSION TRAY

CROSS-REFERENCE TO RELATED APPLICATION

This is a continuation-in-part of U.S. Pat. application Ser. No. 09/302,325, filed on Apr. 29, 1999, and now abandoned.

FIELD OF THE INVENTION

This invention relates generally to dental appliances, and, more particularly, to a gag-preventive dental impression tray.

BACKGROUND OF THE INVENTION

Dental impression trays are used by dentists, orthodontists, prosthodontists and others in the field of dentistry to make models of a patient's teeth or other specific areas of a patient's oral cavity. Dentists and prosthodontists make impressions for the purpose of making false or replacement teeth, or for the preparation of restorative crowns, bridges and the like. Orthodontists make impressions to study malformations of the teeth and jaws and plan a course of treatment. Orthodontists also use impressions to size and manufacture dental appliances.

To obtain a dental model, an impression of desired areas of the patient's mouth is first obtained. To prepare an impression, a quantity of curable dental impression material is placed in an impression tray, and the tray is then positioned in the patient's mouth. The impression material fills and surrounds the selected area of interest of the mouth. Once the impression material has cured, the impression material along with the tray is removed from the mouth. A second curable material is then poured or otherwise placed in the cured impression material. Once the second material has cured, the impression material is removed from the resulting model, which provides an accurate physical replica of the patient's tooth structure and adjacent portions of the patient's gingiva.

A common problem with prior art dental impression trays is that they usually induce a gag reflex when placed in a patient's mouth. This is best appreciated by first understanding the nature of the pharyngeal reflex (gag).

The pharyngeal reflex (gag) is caused by the contraction of the constrictor muscle of the pharynx, elicited by touching the back of the pharynx. In normal swallowing, in the first stage of deglutition, the bolus of food is driven back into the fauces by the pressure of the tongue against the hard palate. At the same time, the base of the tongue is retracted and the larynx raised with the pharynx. During the second stage, the entrance to the larynx is closed by the drawing forward of the arytenoid cartilages toward the cushion of the epiglottis, a movement produced by the contraction of the thyreoarytaenoidei, the arytaenoidi and the arytanoepiglottidei (muscles of the back of the throat). As soon as the bolus of food is received in the pharynx, the elevator muscles relax, the pharynx descends and the constrictors contract upon the bolus and convey it downward into the esophagus.

When a properly designed dental impression tray is placed in the mouth, the second stage of the swallowing response is stimulated as described above by the application of pressure in front of the highly innervated delineation between the hard and soft palate. An improperly designed tray, then, does not apply pressure in front of the delineated space between the hard and soft palate.

A variety of dental impression trays are known in the art. However, none of them are suitable for taking an impression of a patient's maxillary dentition while simultaneously preventing a normal physiological "gag" response to placement of the tray in a patient's mouth. Quite simply, conventional prior art dental impression trays are not designed to prevent a normal gag response which occurs when the tray is placed in a patient's mouth.

One example of a patented dental impression tray is disclosed in U.S. Pat. No. 3,737,663 (White). This patent discloses a set of trays for taking impression of both the maxillary (upper) and mandibular (lower) dentition. Although this patent suggests that one of the patented trays (maxillary) is designed to prevent gagging during use (see, col. 5, lines 10–19), the patented tray is designed to only take an impression of the maxillary dentition, and not the palate.

Another patented maxillary dental impression tray is disclosed in German Patent No. 885,595 (Gruber). Gruber's tray includes an elevated floor portion (see, FIGS. 1–2) and is therefore capable of taking an impression of the patient's palate. However, the arched plan floor of the tray surrounding the elevated portion is open-ended in the back of the tray, which causes the aginate impression material to leak out the back of the tray. Moreover, the elevated portion of the floor has a greater height than the peripheral wall (see, FIG. 2) which causes the tray elevated floor portion to contact the palate during use, and also causes aginate to flow over the peripheral wall, as shown in FIG. 2 of the patent. If the elevated portion of the floor contacts the soft palate, gagging will occur. It does not appear from the patent drawings that the elevated floor section is indented from the posterior wall of the tray to ensure contact only with the hard palate.

What is needed then, is a dental impression tray for the palate and maxillary dentition that will prevent gagging during use.

SUMMARY OF THE INVENTION

The invention broadly comprises a dental impression tray having a continuous peripheral wall, including an anterior section which conforms generally to the anatomy of a person's maxillary dentition, and a posterior section having a height which is substantially less than that of the anterior wall section, and a floor adjoining the continuous peripheral wall, the floor having a substantially flat portion of arched plan shape, and an elevated portion which conforms generally to the anatomy of the person's hard pallet.

A general object of the invention is to provide a dental impression tray which, during use, will not cause a patient to gag.

Another object of the invention is to provide a dental impression tray which is designed to avoid initial contact with a person's soft palate during use, thereby preventing a gag reflex.

A further object of the invention is to provide a dental impression tray for taking impressions of a person's maxillary dentition and soft palate.

These and other objects, features, and advantages of the invention will become apparent to those having ordinary skill in the art upon study of the specification, drawings, and appended claims.

DETAILED DESCRIPTION OF THE PREFERRED EMBODIMENT

At the outset, it should be understood that identical reference numbers on different drawing views identify identical structural elements. Also, although a preferred embodiment of the invention is described herein, it should be apparent that changes and modifications can be made to the invention without departing from the spirit and scope of the invention as claimed.

Figure 1:
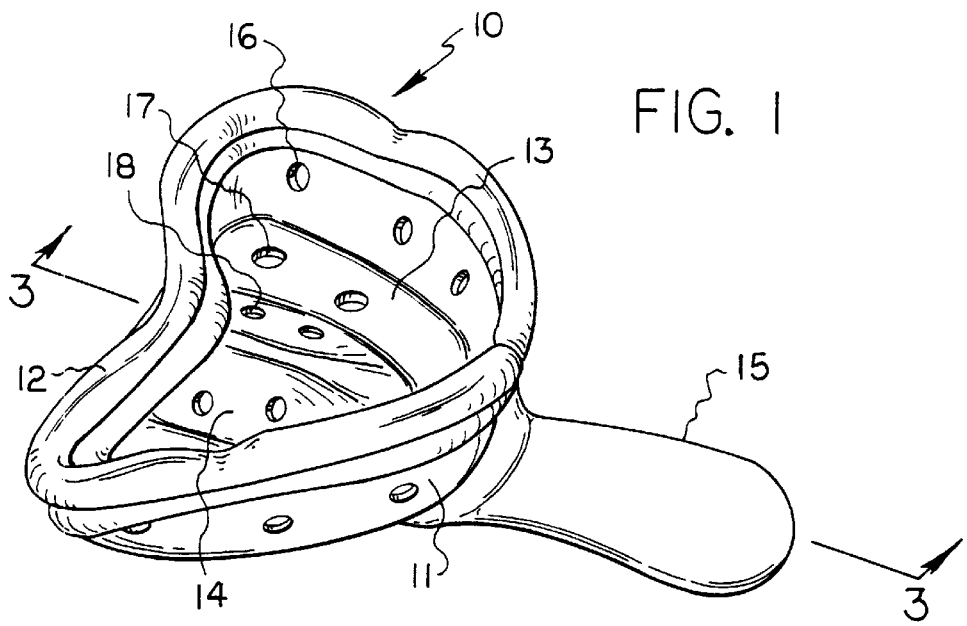
FIG. 1 is a perspective view of the maxillary dental impression tray of the invention.

Adverting now to the drawings, FIG. 1 is a perspective view of the dental impression tray of the present invention. The tray is seen to broadly comprise a continuous peripheral wall having an anterior section 11 which conforms generally to the anatomy of a person's maxillary dentition, and a posterior section 12 having a height p which is substantially less than the height a of the anterior wall section; and a floor adjoining the continuous peripheral wall, the floor having a substantially flat portion 13 of arched plan shape, and an elevated portion 14 which conforms generally to the anatomy of said person's hard pallet 25 (shown in FIGS. 5–8). The anterior wall section includes a plurality of apertures 16, and the posterior wall section includes a plurality of apertures 17. The elevated floor portion 14 includes a plurality of apertures 18. These apertures function to allow the impression material to flow and eliminate air bubbles in the impression.

Figure 2:
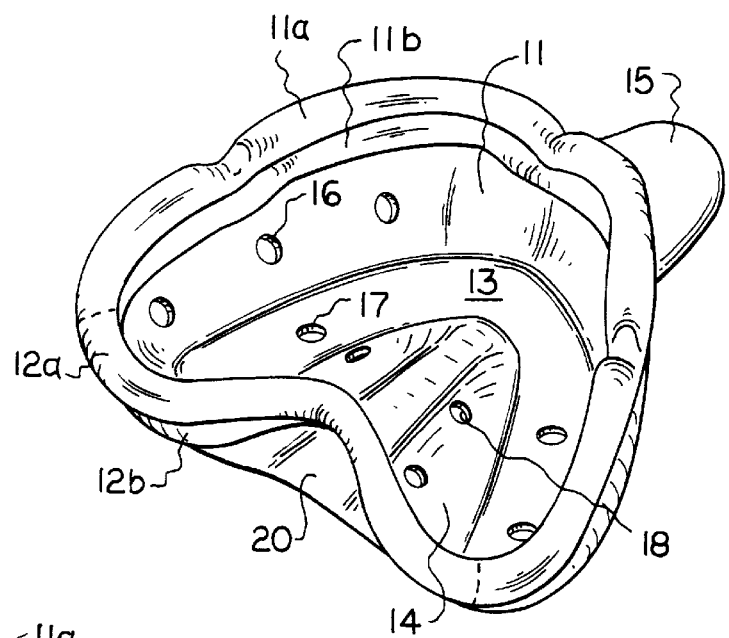
FIG. 2 is a perspective view of the tray of the invention as view from the rear of the tray.
Figure 3:
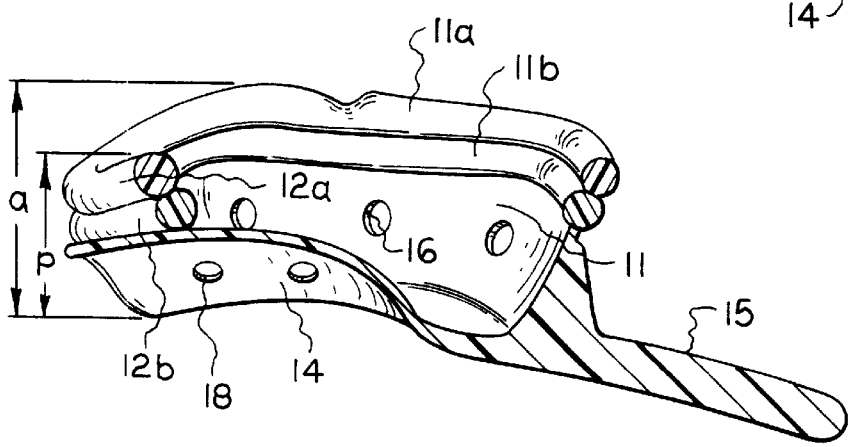
FIG. 3 is a cross-sectional view of the tray taken generally along line 3—3 in FIG. 1.
Figure 4:
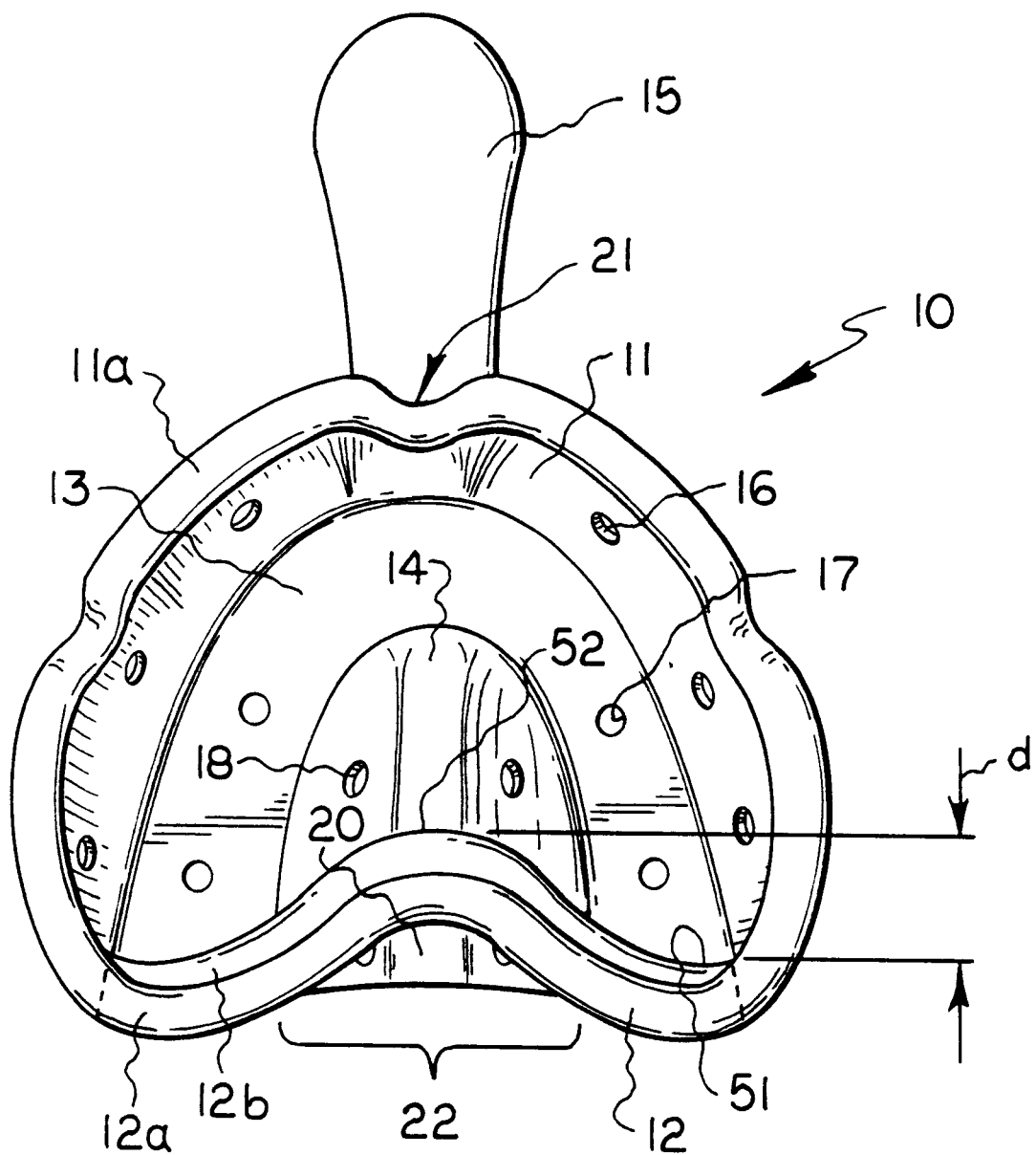
FIG. 4 is a plan view of the dental impression tray of the invention.

Anterior section 11 and posterior section 12 are figuratively separated by dotted lines as shown in FIG. 2. The anterior section is seen to include a rim comprising an upper bead portion 11a and a lower bead portion 11b. The beading begins at the center of the anterior wall section where there exists a "V" shaped notch or cleft. This cleft is necessary to avoid the anterior frenum (a fibrous band of connective tissue covered with mucous membrane, which runs from the lip to the alveolar area of the maxilla at the midline). This allows placement of the anterior wall section of the tray at a sufficient depth to achieve an adequate impression of the dentition and upper jaw and adjacent tissue. The beading continues along the posterior section 12 (shown as upper bead section 12a and lower bead section 12b) in an arcing shape. The bead continues in the center of the posterior wall at indentation 22, another "V" shaped indentation proximate elevated floor section 14, as best shown in plan view in FIG. 4. This notch or indentation accommodates the lateral frenum. Finally, flange 20 extends rearwardly from the base of posterior wall section 12.

Floor section 13 is in a shape that generally matches that of the maxillary dentition of a human being. Similarly, elevated floor portion 14 generally conforms in shape to the hard palate of a person. The side walls of the anterior wall section generally conform to the curve of Spee. The sides slope downward towards the posterior wall. Although the claims of the invention are not limited to specific dimensions, in a preferred embodiment of the invention, the anterior wall has a height a of about 20 millimeters, and the posterior wall has a height p of about 10 millimeters.

The double beading frames the top of the vertical side walls of the anterior wall section (at an approximate height of 15 mm) until the posterior of the tray is reached. At this point the double beading continues in a semi-circular curve along the posterior (2 mm lip) border of the tray (toward the middle) for approximately one-fourth of the width of the posterior wall. At that point, the doubles beading leaves the posterior wall of the tray and is directed forward into the body of the tray (towards the anterior wall) at an angle of approximately 55 degrees with the two beads so placed that the top bead is slightly distal (further back) with respect to the bottom bead, forming an approximate 45 degree angle to the base (floor) of the tray. The double beading continues from each lateral area, in an anterior mesial direction to the midpoint of the tray in an inverted "U" shape (similar to a parabolic form) with the distance of the anterior wall of the inferior (bottom) bead from the posterior bead being about 15 mm at the midline. The diagonal height thus reduces the horizontal distance to the posterior wall to approximately 9 mm. The superior height of the diagonally vertical beading is approximately 8 mm above the floor of the tray at the midpoint of the elevated floor section.

The apertures in the sides and base of the tray allow the impression material to exude in response to the incursion of the teeth, alveolus and palate. The beading acts in molding, containment, and retension of the impression material. The inverted "U" double beading in the posterior wall, because of its position well anterior to the gag trigger area, stimulates that area of the palate to suppress the gag reflex, in a manner similar to the action of swallowing a bolus of food.

Handle 15 is shown as an integral part of the tray. It functions to hold and direct the tray during the taking of an impression. The handle is joined to the tray proximate the floor of the anterior wall, at the middle of the wall section. The handle can be flat or slightly convex in form and varies in width from approximately 20 mm at the base to about 30 mm near its anterior end.

Figure 5:
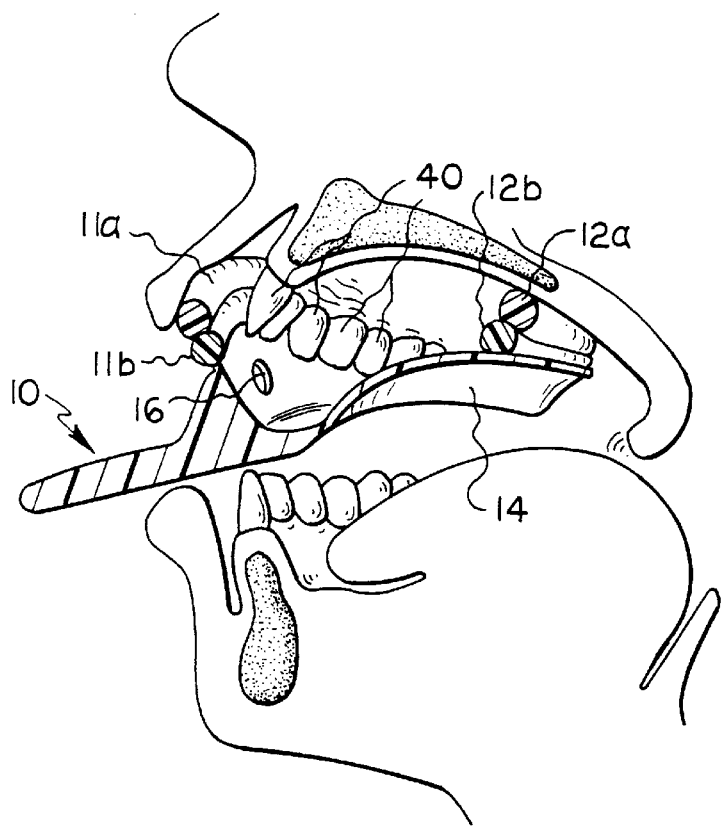
FIG. 5 is a cross-sectional view of the impression tray of the invention inserted into a patient's oral cavity and pivoted upwardly to contact the patient's hard palate, shown not filled with impression material.
Figure 6:
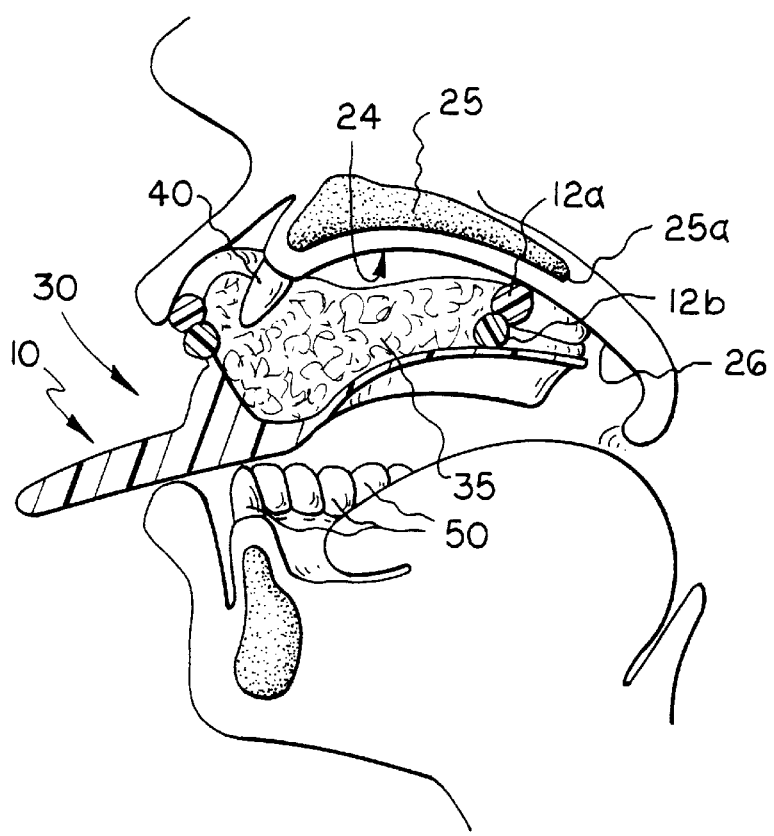
FIG. 6 is a view similar to that of FIG. 5, but showing the impression tray filled with impression material.

The function of the dental impression tray of the invention is illustrated in FIGS. 5–8, respectively. FIG. 5 illustrates the insertion of the tray into the oral cavity, and illustrates the placement and effect of the design of the "U" shape beading in the posterior of the tray. This view is taken with no impression material in the try to clearly show the relationship of the tray to the palate and teeth. As shown in FIG. 5, upper bead 11a of the anterior wall section is tucked under (in back of) upper lip 42 of the patient, and upper bead 12a of the posterior wall section contacts hard palate 25 when pivoted on the front mandibular dentition as shown in FIG. 5. No part of the tray contacts soft palate 26. FIG. 6 is a view similar to that of FIG. 5, except with impression material present in the tray.

Figure 7:
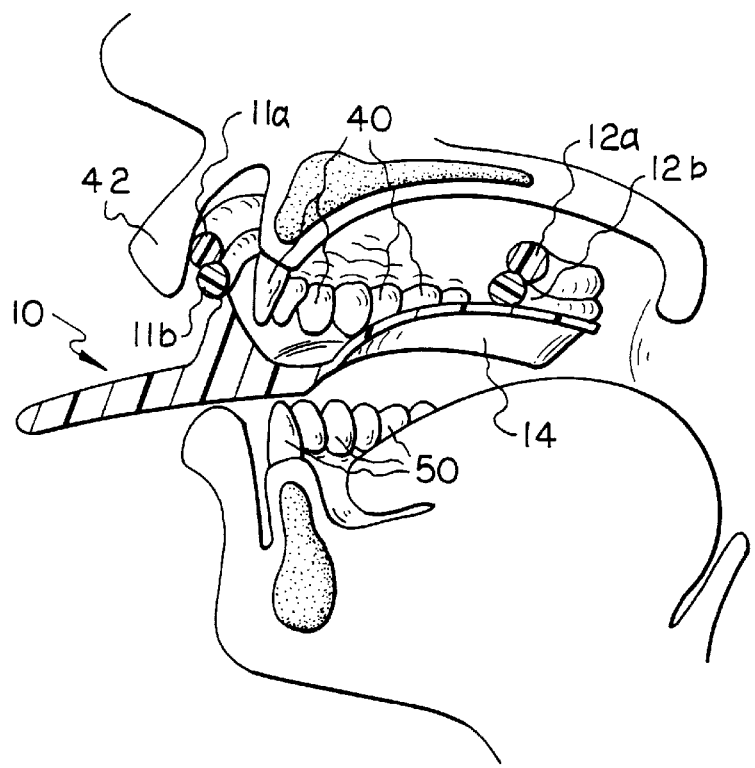
FIG. 7 is a view similar to that of FIG. 5 but with the tray pivoted to a position where the floor of the tray is level and parallel with the occlusal surface of the teeth; and, FIG. 8 is a view similar to that of FIG. 7 but showing the impression tray filled with impression material.
Figure 8:
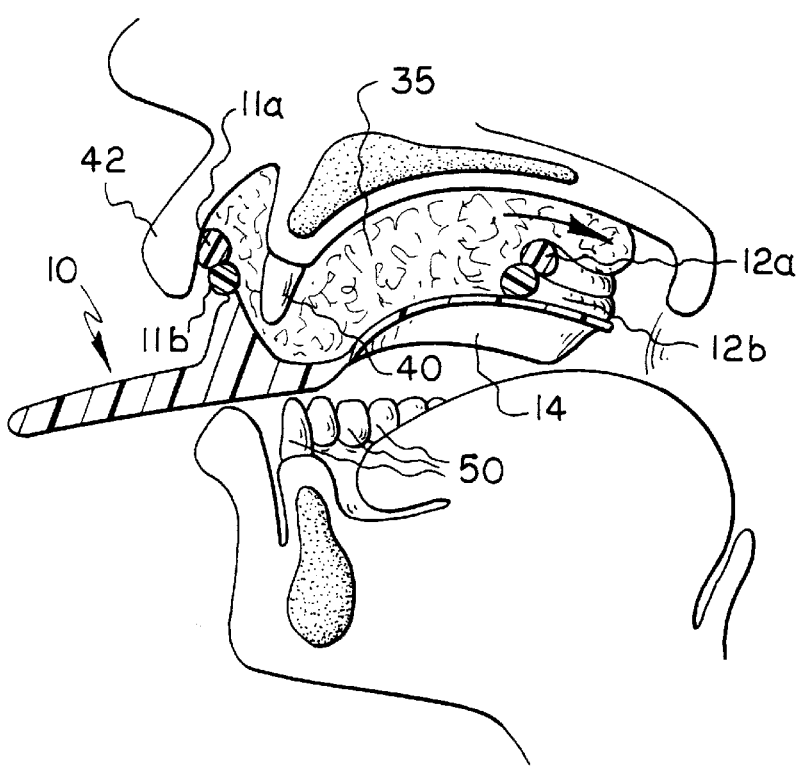

FIG. 7 illustrates the seating of the tray in a front to back motion bringing the base (floor) of the tray level and parallel with the occlusal surface of the teeth. FIG. 8 is a view similar to that of FIG. 7 except with impression material in the tray. This view shows the flow of the impression material toward the posterior of the tray, where it interacts with the inverted "U" beading anterior to the gag reflex trigger area (at the juncture of the hard and soft palates), similar to the action of a bolus of food.

Thus, it is seen that the objects of the invention are efficiently obtained, although changes to the invention should be apparent to those having ordinary skill in the art, without departing from the spirit and scope of the claims.

What I claim is:

1. A dental impression tray comprising:
    a continuous peripheral wall comprising a double bead portion having an upper bead and a lower bead, said wall having an anterior section which conforms generally to the anatomy of a person's maxillary dentition, and a posterior section having a height which is substantially less than that of said anterior wall section; and,
    a floor adjoining said continuous peripheral wall, said floor having a substantially flat portion of arched plan shape, and an elevated portion which conforms generally to the anatomy of said person's hard pallet.

2. A dental impression tray as recited in claim 1, wherein said posterior section includes an indentation protruding towards said anterior section, said indentation adjoining said elevated portion of said floor.

3. A dental impression tray as recited in claim 2 wherein said tray is operatively arranged to take an impression of a person's maxillary dentition and hard palate, including first and second year molars, each of which has a front vertical surface and a rear vertical surface, and wherein said indentation protrudes a distance approximately equal to the distance between the front vertical surface of said first year molar and the rear vertical surface of said second year molar.

4. A dental impression tray as recited in claim 2 wherein said indentation protrudes to a height of approximately six (6) millimeters.

5. A dental impression tray as recited in claim 1 wherein said floor comprises a plurality of apertures therein.

6. A dental impression tray as recited in claim 1 wherein said anterior section of said continuous peripheral wall comprises a plurality of apertures therein.

7. A dental impression tray as recited in claim 1, further comprising a handle extending from said anterior section of said continuous peripheral wall.

8. A dental impression tray as recited in claim 1 wherein said anterior wall section has a height of approximately 20 millimeters as measured from the floor to the top of the anterior wall section.

9. A dental impression tray as recited in claim 1 wherein said posterior wall section has a height of approximately 10 millimeters as measured from the floor to the top of the posterior wall section.

10. A dental impression tray as recited in claim 1 wherein, in the posterior wall proximate said elevated floor section, the lower bead is closer to the anterior wall section than the upper bead, forming an approximate 45 degree angle with respect to the floor section.

* * * * *